(12) United States Patent
Hunter et al.

(10) Patent No.: US 8,355,767 B2
(45) Date of Patent: Jan. 15, 2013

(54) RAMAN SPECTROSCOPY FOR NON-INVASIVE GLUCOSE MEASUREMENTS

(75) Inventors: Martin Hunter, Bradford, MA (US);
Annika Enejder, Göteborg (SE);
Thomas Scecina, Medfield, MA (US);
Michael Feld, Jamaica Plain, MA (US);
Wei-Chuan Shih, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1781 days.

(21) Appl. No.: 11/412,418

(22) Filed: Apr. 27, 2006

(65) Prior Publication Data

US 2007/0060806 A1    Mar. 15, 2007

Related U.S. Application Data

(60) Provisional application No. 60/675,252, filed on Apr. 27, 2005.

(51) Int. Cl.
*A61B 5/1455* (2006.01)
(52) U.S. Cl. ...................................................... 600/316
(58) Field of Classification Search ................ 128/633, 128/664, 665; 356/39, 301; 600/309–344
See application file for complete search history.

(56) References Cited

U.S. PATENT DOCUMENTS

| | | | |
|---|---|---|---|
| 4,975,581 A | 12/1990 | Robinson et al. |
| 5,355,880 A | 10/1994 | Thomas et al. |
| 5,435,309 A | 7/1995 | Thomas et al. |
| 5,481,113 A | 1/1996 | Dou et al. |
| 5,494,032 A | 2/1996 | Robinson et al. |
| 5,615,673 A | 4/1997 | Berger et al. |
| 5,630,413 A | 5/1997 | Thomas et al. |
| 5,754,289 A | 5/1998 | Ozaki et al. |
| 5,842,995 A | 12/1998 | Mahadevan-Jansen et al. |
| 5,857,462 A | 1/1999 | Thomas et al. |
| 6,044,285 A | 3/2000 | Chaiken et al. |
| 6,064,897 A | 5/2000 | Lindberg et al. |
| 6,070,093 A | 5/2000 | Oosta et al. |
| 6,167,290 A | 12/2000 | Yang et al. |
| 6,181,957 B1 | 1/2001 | Lambert et al. |
| 6,197,503 B1 | 3/2001 | Vo-Dinh et al. |

(Continued)

FOREIGN PATENT DOCUMENTS

WO    WO 96/29925    10/1996

OTHER PUBLICATIONS

Mobley et al., "Single-board computer based control system for a portable Raman device with integrated chemical identification," American Institute of Physics, Review of Scientific Instruments, vol. 75, No. 6, Jun. 2004.

(Continued)

*Primary Examiner* — Eric Winakur
*Assistant Examiner* — Marjan Fardanesh
(74) *Attorney, Agent, or Firm* — McCarter & English LLP

(57) ABSTRACT

The present invention relates to the use of Raman spectroscopy for quantitative, non-invasive transcutaneous measurement of blood analytes, such as glucose. Raman spectroscopy is used to measure glucose transcutaneously, in patients whose blood glucose levels were monitored. Raman spectra were collected transcutaneously along with glucose reference values provided by standard capillary blood analysis. A partial least squares calibration was created from the data from each subject and validated using leave-one-out cross validation.

26 Claims, 13 Drawing Sheets

U.S. PATENT DOCUMENTS

| | | | |
|---|---|---|---|
| 6,331,892 B1 * | 12/2001 | Green | 356/451 |
| 6,377,828 B1 | 4/2002 | Chaiken et al. | |
| 6,424,850 B1 | 7/2002 | Lambert et al. | |
| 6,494,576 B1 | 12/2002 | L'Esperance, Jr. | |
| 6,522,903 B1 | 2/2003 | Berman et al. | |
| 6,560,478 B1 | 5/2003 | Alfano et al. | |
| 6,567,678 B1 | 5/2003 | Oosta et al. | |
| 6,574,501 B2 | 6/2003 | Lambert et al. | |
| 6,621,614 B1 * | 9/2003 | Zhang | 359/260 |
| 6,662,030 B2 | 12/2003 | Khalil et al. | |
| 6,687,620 B1 | 2/2004 | Haaland et al. | |
| 6,690,966 B1 | 2/2004 | Rava et al. | |
| 6,721,582 B2 | 4/2004 | Trepagnier et al. | |
| 6,842,702 B2 | 1/2005 | Haaland et al. | |
| 6,922,645 B2 | 7/2005 | Haaland et al. | |
| 7,226,166 B2 * | 6/2007 | Della Vecchia et al. | 351/221 |
| 7,505,128 B2 | 3/2009 | Zribi et al. | |
| 2003/0144582 A1 | 7/2003 | Cohen et al. | |
| 2003/0176777 A1 | 9/2003 | Muller-Dethlefs | |
| 2003/0227628 A1 | 12/2003 | Kreimer et al. | |
| 2004/0039269 A1 | 2/2004 | Ward et al. | |
| 2005/0010090 A1 | 1/2005 | Acosta et al. | |
| 2005/0027176 A1 | 2/2005 | Xie | |
| 2005/0030657 A1 | 2/2005 | Maier et al. | |
| 2005/0043597 A1 | 2/2005 | Xie | |
| 2006/0240401 A1 | 10/2006 | Clarke et al. | |
| 2008/0306363 A1 | 12/2008 | Chaiken et al. | |
| 2009/0073432 A1 | 3/2009 | Jalali et al. | |

OTHER PUBLICATIONS

Robinson et al., "Noninvasive glucose monitoring in diabetic patients: a preliminary evaluation," Clinical Chemistry, vol. 38, No. 9, 1618-1622, 1992.

Gerard L. Cote, "Noninvasive and minimally-invasive optical monitoring technologies," Journal of Nutrition, vol. 131, No. 5, 1596S-1604S, 2001.

Malin et al., "Noninvasive prediction of glucose by near-infrared diffuse reflectance spectroscopy," Clinical Chemistry, 45:9, 1651-1658, 1999.

Burmeister et al., "Evaluation of measurement sites for noninvasive blood glucose sensing with near-infrared transmission spectroscopy," Clinical Chemistry, 45:9, 1621-1627, 1999.

Omar S. Khalil, "Spectroscopic and clinical aspects of noninvasive glucose measurements," Clinical Chemistry, 45:2, 165-177, 1999.

Sacks et al., "Guidelines and recommendations for laboratory analysis in the diagnosis and management of diabetes mellitus," Clinical Chemistry, 48:3, 436-472, 2002.

Yeh et al., "Monitoring blood glucose changes in cutaneous tissue by temperature-modulated localized reflectance measurements," Clinical Chemistry, 49:6, 924-934, 2003.

Tae-Woong Koo, "Measurement of blood analytes in turbid biological tissue using near-infrared Raman spectroscopy," MIT 2001.

* cited by examiner

RAMAN SPECTROSCOPY FOR NON-INVASIVE GLUCOSE MEASUREMENTS

CROSS REFERENCE TO RELATED APPLICATIONS

This application claims the priority of U.S. Provisional Application No. 60/675,252, filed Apr. 27, 2005, the whole of which is hereby incorporated by reference herein.

STATEMENT REGARDING FEDERALLY SPONSORED RESEARCH OR DEVELOPMENT

This invention was made with government support under grant number P41 RR002594 awarded by the National Institutes of Health. The government has certain rights in this invention.

BACKGROUND OF THE INVENTION

It is estimated that the number of people afflicted with diabetes will increase by 46% worldwide from 2000 to 2010. There are many long-term complications, the most significant being cardiovascular, retinal, renal and neuropathic. The control of blood glucose levels, which currently entails frequent blood sampling, significantly delays occurrence of these complications, resulting in improved quality of life and reduced burden on the health care system. Conventional blood sampling methods are painful and have other undesirable features. Non-invasive ("transcutaneous") blood sampling methods are an attractive alternative for monitoring glucose, as well as other blood analytes. Of the in vivo measurements reported for a variety of non-invasive techniques, none has demonstrated sufficient accuracy for non adjunctive clinical use. In addition, there has been no substantial verification that the measured signals result from the actual glucose concentrations. Instead, it has been shown that the calibration models derived easily become over-determined, and that chance correlations are picked up as variations in glucose concentrations. This indicates the need for a non-invasive method providing greater specificity.

SUMMARY OF THE INVENTION

The present invention relates to systems and methods using Raman spectroscopy for transcutaneous monitoring of glucose concentrations and other blood analytes. Raman spectra exhibit distinct narrow features characteristic of the molecules present in the blood-tissue matrix, including glucose. Despite its weak signals, Raman spectroscopy has been shown to provide detailed quantitative information about the chemical composition of skin such as the measurement of proteins and lipids.

To perform accurate and repeatable transdermal measurements of glucose and other analytes requires improvements in the signal to noise ratio to compensate for the difficulties in acquiring weak Raman signals within the complex spectrum found in human skin. By improving the size and resolution of the imaging device, increasing the number of optical fibers used for coupling the collected signal for detection, the use of a sidelooking parabolic mirror for light delivery and collection and a method for curvature correction during binning of pixels, substantial improvements in signal to noise ratio have been obtained. In achieving signal to noise ratios in excess of 2000, and preferably greater than 4000 in measurements through human skin, repeatable and verifiable measurements of blood glucose and other analytes such as urea, total protein, albumin, triglycerides, hematocrit and hemoglobin can be obtained. Signal to noise ratios in excess of 6000 have been obtained and are preferably employed to minimize error.

Because spectra from blood or tissue are composed of contributions from many constituents, extraction of quantitative information can involve the use of a reliable multivariate calibration method, such as partial least squares (PLS) regression analysis. PLS analysis of Raman spectra has been successfully applied to quantitative measurements of glucose and other analytes in serum and whole blood samples. See, for example, U.S. Pat. No. 5,615,673 and PCT/US96/04136, the entire contents of this patent and application being incorporated herein by reference.

DETAILED DESCRIPTION OF THE INVENTION

Figure 1A:
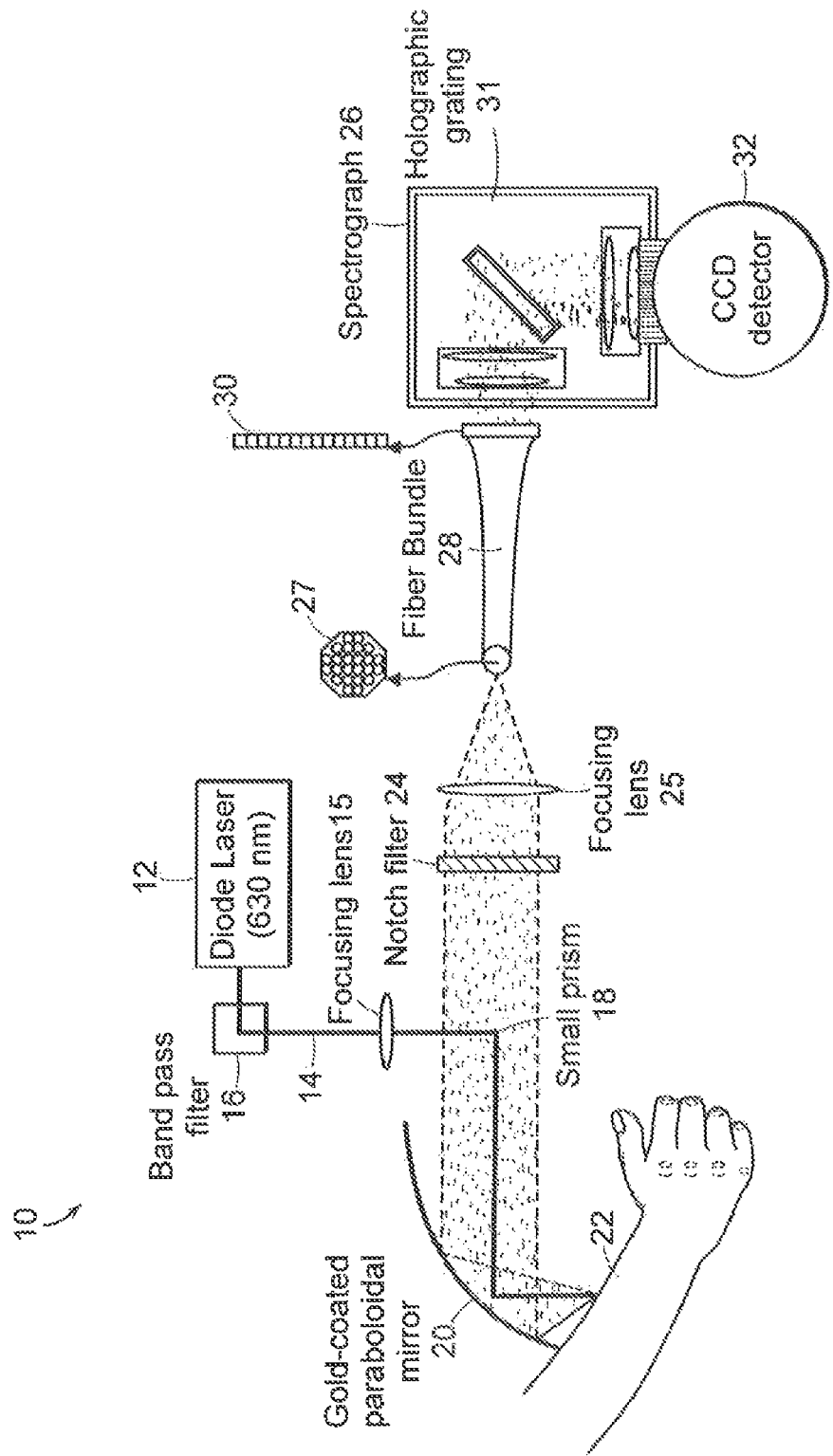
FIG. 1A is a schematic illustration of a light delivery and collection system in accordance with a preferred embodiment of the invention.

Raman spectra were obtained using a system to collect Raman light emitted from the skin of a patient with high efficiency. The system shown in FIG. 1A used a light source 12 such as a 830 nm diode laser (PI-ECL-830-500, Process Instruments, Salt Lake City, Utah) as the Raman excitation source. The beam 14 was passed through a bandpass filter 16 (Kaiser Optical Systems, Ann Arbor, Mich.), directed toward a paraboloidal mirror 20 (Perkin Elmer, Azusa, Calif.) by means of a lens 15 and a small prism 18, and focused onto the forearm 22 of a human subject with an average power of 300 mW and a spot area of ~1 mm$^2$. Backscattered Raman light was collected by the mirror 20 and passed through a notch filter 24 (Super Notch Plus, Kaiser Optical) to reject the backscattered Rayleigh peak and the specular reflection at 830 nm. The filtered light was transferred to a spectrometer (Holospec f/1.4i or f/1.8i, Kaiser Optical) by means of a lens 25 and an optical fiber bundle 28 (Romack Fiber Optics, Williamsburg, Va.), which converted the circular array 27 of the collected light to a single row 30 of fibers, in order to match the shape of the spectrometer entrance slit. The fiber optic coupler 28 preferably has at least 50 optical fibers, and in this example has 65 fibers each being 396 µ in diameter with a numerical aperture of 0.37. The spectra were collected from the grating 31 by a cooled CCD array detector 32 (1340× 1300 pixels, Roper Scientific, Trenton, N.J.) corrected for the image curvature in the vertical direction caused by the spectrometer optics and grating and then binned in the vertical direction, resulting in a 1340 pixel spectrum. By employing a binning pixellated detector having at least 1,000,000 pixels or more, a substantial improvement in signal to noise ratio is provided.

Figure 1B:
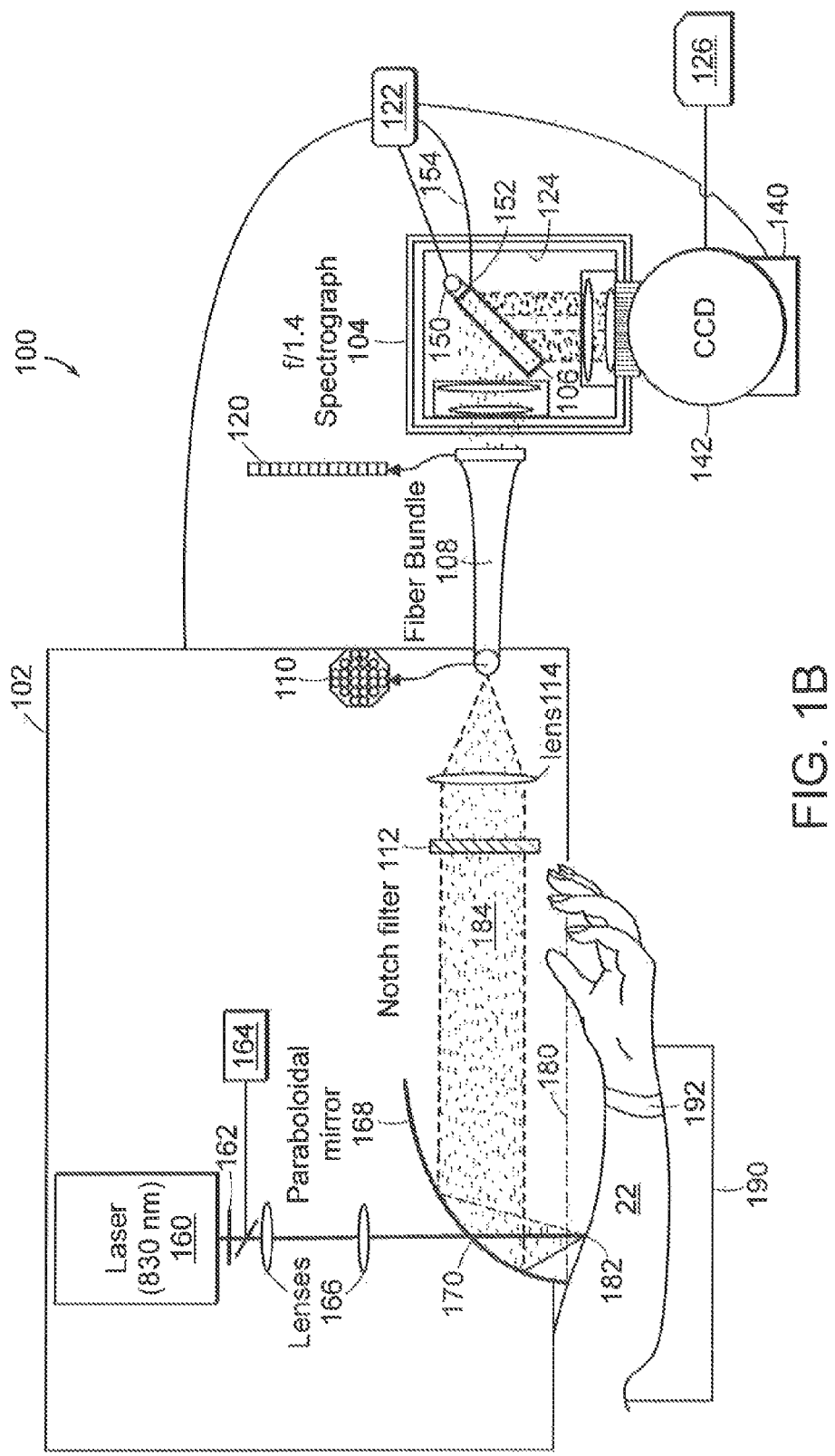
FIG. 1B schematically illustrates another preferred embodiment of the invention.

Another preferred embodiment 100 is shown in FIG. 1B where the light source 160, mirror 168 and associated optics are contained within a collector housing 102. The source directs a beam through a narrow pass filter 162. A mirror can be used to sample the beam for a detector 164 that can be used to monitor beam stability. The source 160 and detector 164 can be connected to system controller 122. Lenses 166 deliver the beam through an aperture 170 in the mirror 168 onto the tissue region of interest 182. The region 182 is "off axis", outer of the collector housing, i.e., it is positioned outside the longitudinal axis 180 which runs parallel to the reflected light axis 184 that returns from region 182 on the arm or other location 22 on the patient.

A holder 190 is used to rigidly hold the arm 22 of the patient in one position relative to the mirror 168 during each measurement. A restraint 192 can be used near or in combination with the region 182 to stabilize the arm, finger or other sampling location on the patient.

A notch filter 112 and lens 114 direct the light reflected by mirror 168 onto the input of a two dimensional array 110 of a fiber coupler 108. The output single row array 120 is coupled to the entrance slit of a spectrograph housing 104. the housing 104 can have an insulated cover 124, a dispersing element such as a grating 106, a temperature sensor 150, a temperature control element 152 such as a heating element that is connected 154 to system controller 122. The controller 122 can also control a thermoelectric cooler 140 for the pixellated detector 142. The detector 142 is connected to a processor 126 with a memory. The processor 126 is programmed to process spectral data from the detector to determine quantitative values for the concentrations of blood analytes in tissue as described in detail herein.

Temperature and optical monitoring and feedback control systems are used to stabilize the light source and detector systems to provide calibrated repeatable measurement of blood analytes with a signal to noise ratio in the resulting data that accurately measures blood glucose concentration in the tissue, for example.

In the following example, Raman spectra were collected from the forearms of 20 healthy human subjects following the intake of 220 ml of a glucose-rich beverage (SUN-DEX). The data from three of the subjects were not included in the analysis because of problems such as excessive movement during the measurement. Using the data from the remaining 17 subjects, each spectrum was formed by averaging 90 consecutive two-second acquisitions (three minute collection times). Spectra were acquired every five minutes over a period of 2 to 3 hours (2.3 hours, on average), forming a "measurement series" for each subject (27 spectra per series, on average). During this period, the blood glucose concentration typically doubled and then returned to its initial value. During the measurements, reference capillary blood samples were collected every ten minutes (277 total) and analyzed by means of a Hemocue glucose analyzer, with a one SD precision specified by the manufacturer as ≦6 mg/dL. Spline interpolation was used to provide reference values at five minute intervals.

Raman spectra in the range of 355-1545 cm$^{-1}$ were selected for processing. Spectra collected in vivo consisted of large, broad backgrounds superposed with small, sharp Raman features. Two methods of processing were used for the collected spectra. In the first method, the background was removed by least-squares fitting each spectrum to a fifth order polynomial and subtracting this polynomial from the spectrum, leaving the sharp Raman features. In the second method, the spectra were analyzed without removal of the background. Removing the background offers the advantage of more clearly showing the Raman spectra. All of the Raman spectra illustrated in the figures were pre-processed in this way. However, somewhat more accurate calibrations were obtained using data without the background removed (mean absolute error of 7.2% vs. 9.2%). Intensity decreases and spectral shape changes in the background signal were observed in the measurements on each subject. The effect of the polynomial subtraction method on Raman spectra extracted from background signals with these changes may cause an increase in error with background removed. Therefore, the performance results presented later are based upon measured spectra without background removal.

The features of the observed in vivo Raman spectra were seen to be dominated by spectral components of human skin. These contributions were evaluated by least-squares fitting the observed Raman spectra to Raman spectra of the key constituents: human callus skin (thickened stratum corneum with high keratin content), collagen I and III to model dermal and epidermal structural protein, and triolein (a triglyceride) to model subcutaneous fat. A Raman spectrum of human hemoglobin was also included to account for the blood volume probed. The spectra of other possible components, such as water, cholesterol, elastin, phosphatidylcholine and actin, were also included. The spectrum for each component was normalized by its total Raman signal strength.

For the data set from each subject of the in vivo measurements, the combined background/Raman spectra were analyzed by means of partial least squares regression. The spectra were smoothed with a 13 point Savitsky-Golay algorithm to increase the effective signal to noise ratio and then mean centered. A PLS calibration was created and validated using leave-one-out cross validation. A PLS calibration regression vector was formed from between 2 and 10 loading vectors from each calibration set. The predicted glucose concentrations were then obtained as the scalar product of the measured Raman spectra and the calibration regression vector plus the mean value of reference glucose concentrations. A mean absolute error (MAE) was calculated for the predicted glucose concentrations of the n samples in each data set as:

$$MAE = \frac{1}{n}\sum_{i=1}^{n} \text{Abs}((glu_{meas} - glu_{ref})/glu_{ref}) \quad (1)$$

Figure 2:
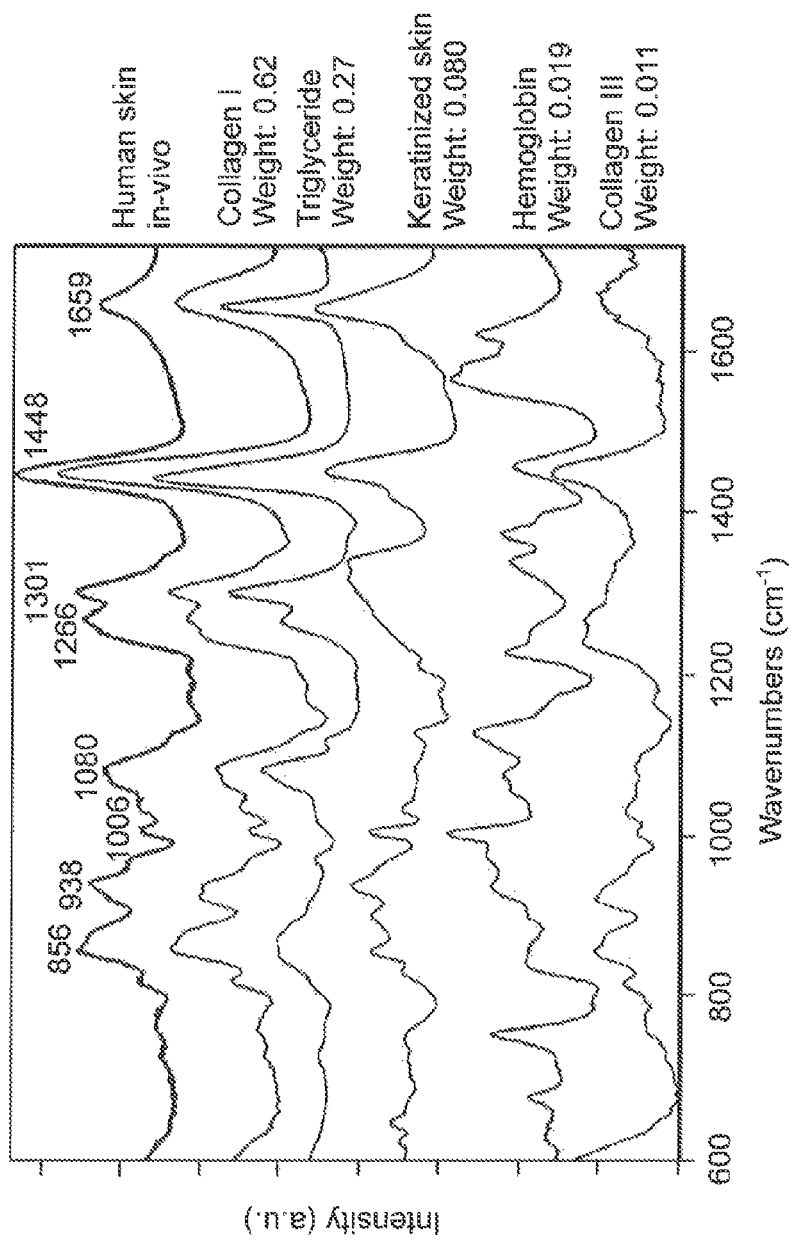
FIG. 2 shows Raman spectra of human skin and it is primary chemical components; average weight coefficients, generated by means of least-squares-fits of the component spectra to the 461 Raman spectra from the 17 subjects, are listed on the right; the prominent peaks are indicated.

FIG. 2 compares a typical Raman spectrum from the forearm of a subject to the Raman spectra of the primary chemical components of the superficial layers of human skin (epidermis, dermis and subcutaneous fat). From visual inspection, as well as by fitting the spectral components to the in vivo spectra, the dominant spectral feature was found to be collagen I, the main component of dermis. A percentage weight coefficient of 0.62±0.08 was obtained, averaged over the 461 in vivo spectra. This is more than twice that found for the second largest component, triolin (0.27±0.13), characteristic of subcutaneous fat. Keratinized tissue (0.08±0.06), hemoglobin (0.019±0.01) and collagen III (0.011±0.02) all contributed to a lesser extent. The contribution of water, cholesterol, elastin, phosphatidylcholine and actin, were all found to be insignificant. The large standard deviations reflect the variations in chemical composition among subjects, whereas within each measurement series the component weight coefficients were relatively constant (standard deviations an order of magnitude lower).

Figure 3A:
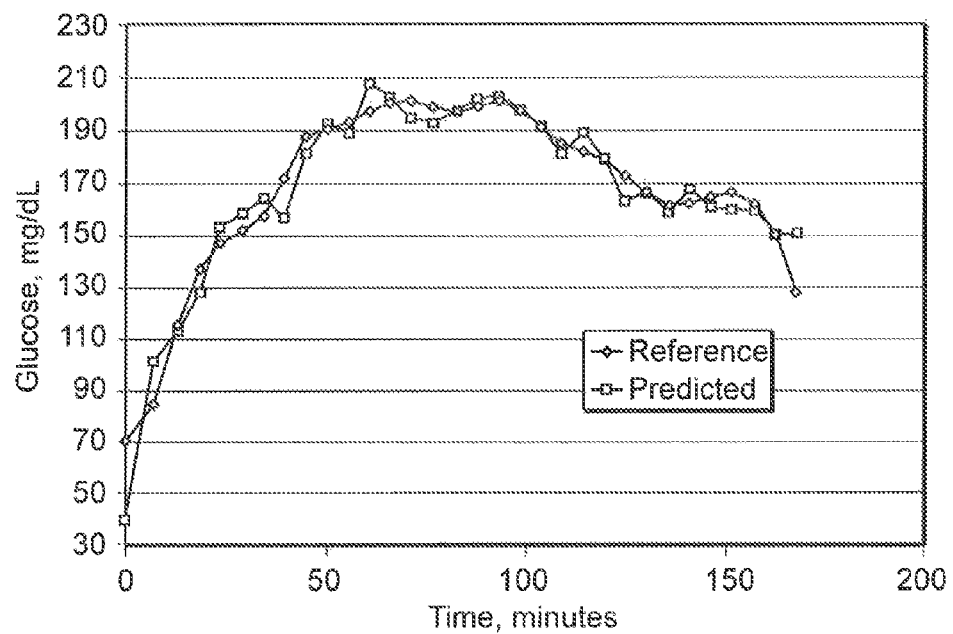
FIG. 3 includes left (a) chart shows the predicted glucose tracking the reference values for one volunteer; and the predicted vs. the reference of the same data is shown on the right (b), with a mean absolute error of 5.0% and an $R^2$ of 0.93.
Figure 3B:
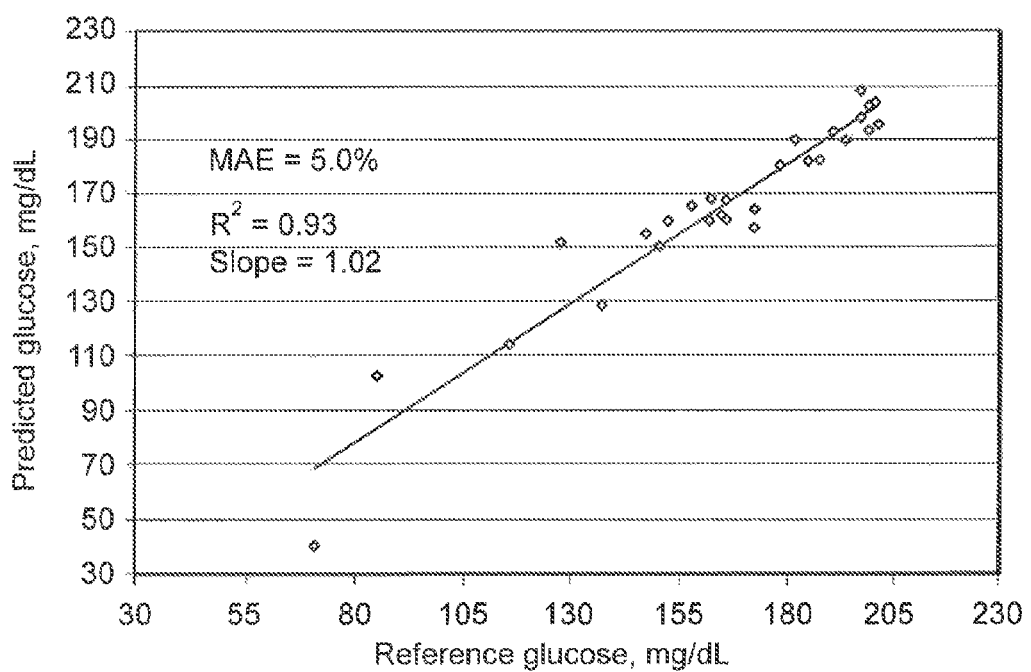

A comparison of the predicted glucose concentrations to the corresponding reference data from one of the subjects is shown in FIG. 3. The mean absolute error (MAE) in the validated data is 5.0% with an $R^2$ of the 0.93.

This procedure was applied individually to data from each of the objects. A summary of the results of cross validated calibration the data set from each subject is shown in Table 1. Although the example in FIG. 3 shows the calibration with the lowest MAE, the calibrations for many other subjects are also good, as can be seen in Table 1.

| Subject | R2 | MAE | Factors | No. of Samples | Regression vector correlation with glucose |
|---|---|---|---|---|---|
| 1 | 0.93 | 5.0% | 9 | 32 | 0.31 |
| 2 | 0.92 | 6.2% | 7 | 27 | 0.14 |
| 3 | 0.92 | 6.9% | 9 | 27 | 0.28 |
| 4 | 0.91 | 6.9% | 9 | 25 | −0.03 |
| 5 | 0.89 | 6.5% | 8 | 26 | 0.41 |
| 6 | 0.89 | 7.0% | 7 | 28 | 0.20 |
| 7 | 0.87 | 9.0% | 3 | 26 | 0.06 |
| 8 | 0.87 | 8.5% | 8 | 30 | 0.33 |
| 9 | 0.85 | 7.0% | 10 | 25 | 0.20 |
| 10 | 0.83 | 8.4% | 7 | 25 | 0.29 |
| 11 | 0.83 | 8.1% | 6 | 20 | 0.21 |
| 12 | 0.79 | 5.2% | 3 | 25 | 0.06 |
| 13 | 0.77 | 8.2% | 7 | 30 | 0.12 |
| 14 | 0.74 | 10.2% | 9 | 31 | 0.10 |
| 15 | 0.74 | 7.2% | 8 | 28 | 0.12 |
| 16 | 0.66 | 10.4% | 6 | 29 | 0.27 |
| 17 | 0.65 | 11.6% | 8 | 26 | 0.12 |
| Mean | 0.83 | 7.8% | 7.3 | 27.1 | 0.2 |

Figure 4:
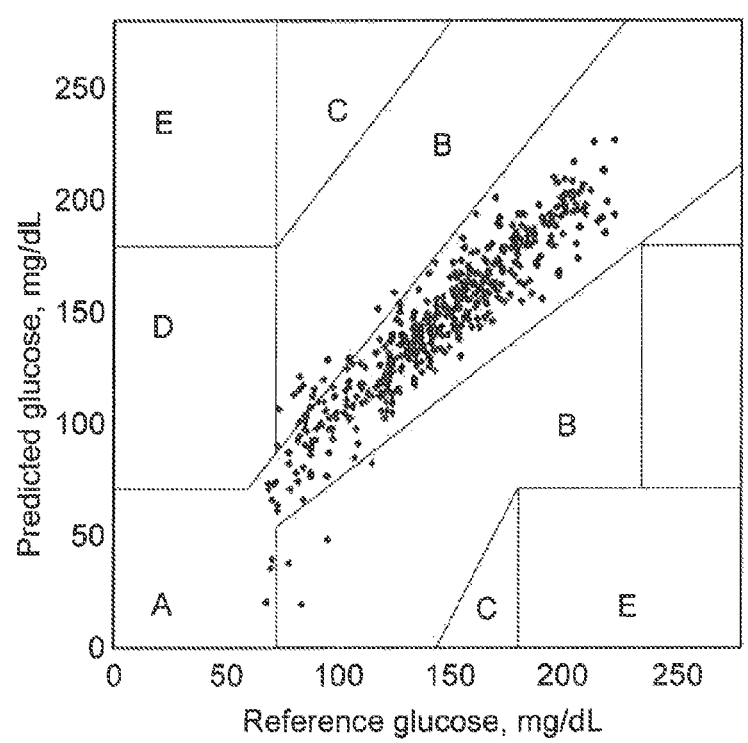
FIG. 4 illustrates cross validated results for 17 subjects calibrated individually shown for convenience on a Clark Error Grid. The average prediction error for this set is 7.7% and the $R^2$ is 0.87.

The cross validated calibration results from each of the 17 subjects combined into one chart are shown in FIG. 4. For the data from all 17 subjects, the mean absolute error is 7.7% and the $R^2$ is 0.87.

Figure 5:
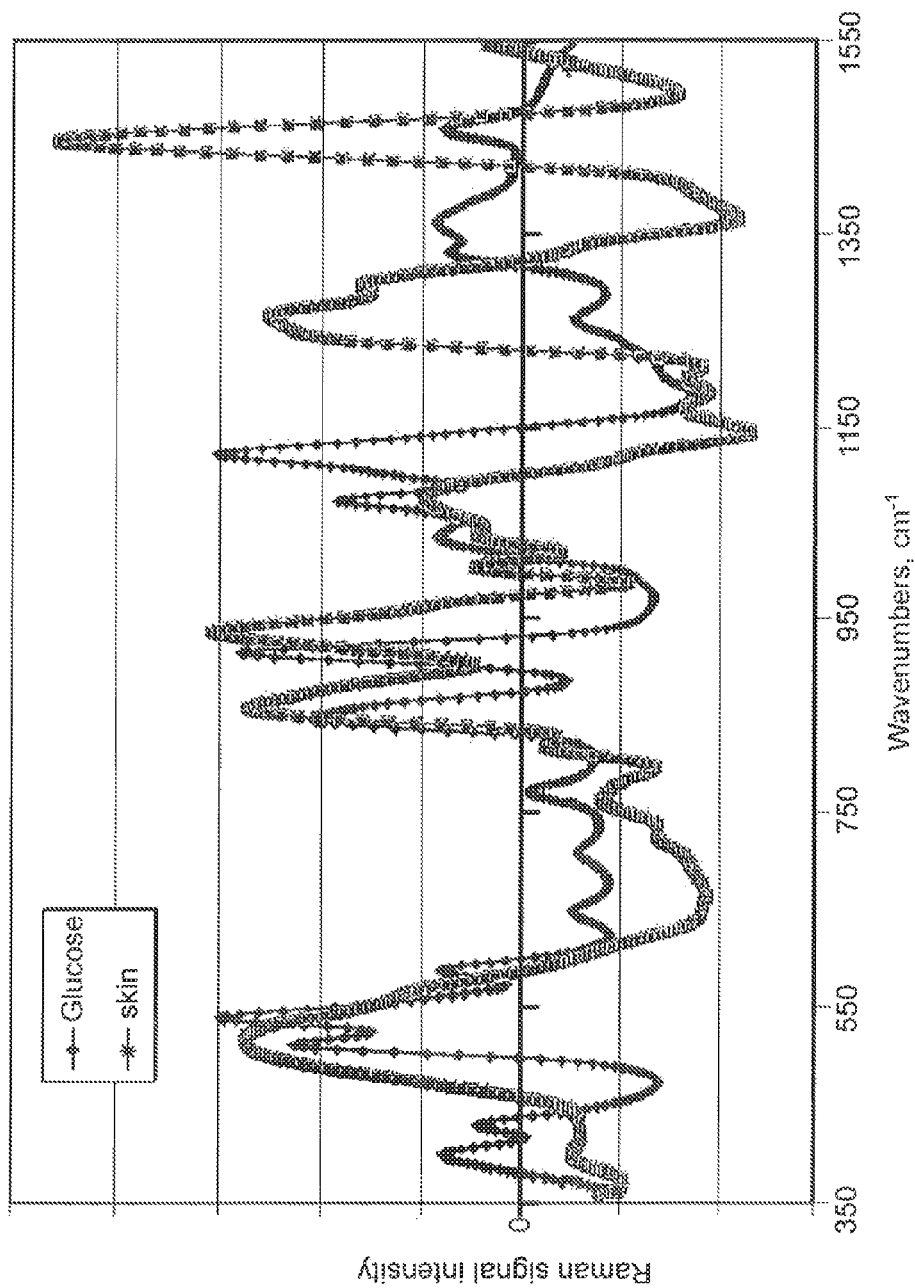
FIG. 5 illustrates a Raman spectrum of glucose in water compared to a typical spectrum of human skin, scaled to fit on the same chart; the spectra are centered about the horizontal axis as a result of the background removal process.

The ability to non-invasively monitor variations in glucose present at low concentrations in the blood-tissue matrix of skin, a complex molecular medium, requires a sensitive and highly specific method. Raman spectroscopy provides such a method because of its sharp, characteristic spectral features. The fact that the multiple peaks of the Raman spectrum of glucose are distinct from those of human skin tissue (FIG. 5) supports the ability to differentiate changes in glucose from changes in tissue characteristics.

In order to measure glucose concentrations in human skin, it is desirable to sample the innermost skin layer, the viable dermis, which is well supplied by glucose from its capillary network. Evidence that the dermis is being sampled is provided by the fact that the Raman spectra collected from the forearms of the subjects are dominated by collagen (approximately 90% of the total protein content, according to a least-squares fit), the major component of dermis. Its contribution is much stronger than that of the keratinized outermost skin layer. The underlying subcutaneous fat is also sampled, as evidenced by the fact that triglyceride is the second largest contribution to the skin spectrum. Comparison with the Raman spectrum of subcutaneous fat indicated that triglycerides are the major Raman scatters in adipose tissue. This establishes that the sampling depth extends beyond the dermis. Also noteworthy is the small but significant contribution from hemoglobin.

The calibrations are good for many subjects, with 11 of the subjects having an $R^2$ of over 0.8 and a mean absolute error of 9% or less. All but two of the subjects had an $R^2$ of more than 0.7.

One issue is whether the calibration is based upon glucose. This issue is relevant to many non-invasive measurement technologies and particularly to a protocol like a glucose tolerance test and where no independent data is available. It is possible that variations specific to an individual or instrument that happen to be correlated with the glucose concentrations can dominate the calibration.

Figure 6:
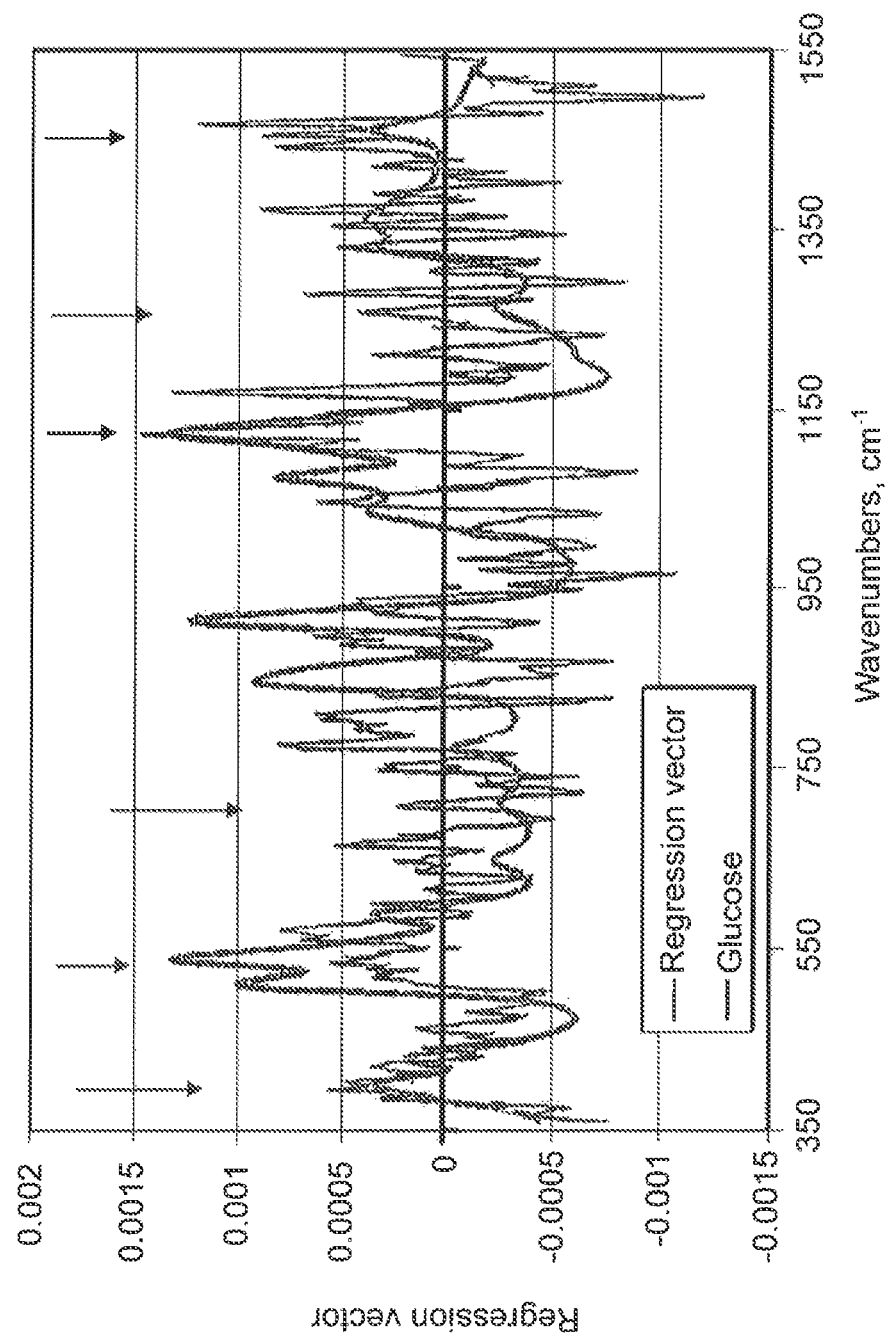
FIG. 6 illustrates the regression for the calibration shown in FIG. 3 and the spectrum of glucose, scaled to fit on the same chart; numerous peaks in the glucose spectrum match peaks in the regression vector, as shown by the arrows, indicating that glucose is contributing to the calibration.

Raman spectroscopy offers a unique way to address this issue. Due to the sharp features of Raman spectra, it is possible to assess the importance of glucose in the calibration by comparing the calibration regression vector to the spectrum of glucose. As an example, FIG. 6 compares the regression vector for the calibration shown in FIG. 3 to the spectrum of glucose in water, scaled to fit on the same chart. The fact that numerous glucose spectrum peaks appear in the regression vector indicates that the glucose variation is indeed captured in this calibration. This correlation between the regression vector and the spectrum of glucose is an indication of the importance of glucose in the calibration. This correlation is not expected to be close to 1 because the regression vector also includes spectral contributions from interferents. In the example of FIG. 6, the correlation is 0.31. This signifies that glucose is an important component in this calibration.

The appearance of glucose peaks in the regression vector and the correlation between it and the glucose spectrum is not as strong for all subjects as is shown in the previous example. These results indicate that the correlation of the regression vector with the glucose spectrum is another factor along with MAE, $R^2$ and slope with which to judge the quality of calibrations for Raman measurements.

Use of the correlation of the regression vector with the glucose spectrum as an additional metric with which to judge the quality of calibrations has helped us improve some of the calibrations. In the calibrations for four of the subjects (2, 11, 13, and 17), the numbers of factors having the lowest standard error of validation (SEV) were 2, 3, or 4. The regression vectors generated by the use of these numbers of factors had a very low correlation (even negative in some) to the glucose spectrum. By increasing the number of factors beyond the point of lowest SEV significantly improved the correlation with glucose. This change brought the numbers of factors more in line with calibrations on other subjects. In these cases, calibrations with a higher correlation with glucose, even though they have a higher SEV, are more strongly influenced by glucose. Also for 2 subjects (7 and 12), where the optimum number of factors is 3, increasing the number of factors does not increase a low correlation (0.06 in both cases) to glucose. The MAE's and $R^2$'s for these calibrations are in the same range as those for other subjects. However, the low correlations with glucose suggest that these calibrations may be based in part at least, upon spurious factors. The calibration for subject 4 also appears good, as judged by an MAE of 6.9% and an $R^2$ of 0.91. However a −0.03 correlation between its regression vector and glucose suggest that this calibration is also based upon spurious factors.

Additionally indications of glucose playing an influential role in the calibrations is seen by examining the results of calibrations formed by combining data sets from a number of subjects together, as in the following procedure.

Data from a number of subjects were combined into one set. A calibration sequence was generated for the entire set and validated by leave-one-out cross validation. The mean absolute error rises as data from more subjects is added to the reference data set because the different chemical and physical characteristics among various people increase the spectral variability. However, a limited rise indicates that the signal from the common variable, glucose, is strong enough to be seen among other variations. Through simulation and in vitro measurements, the correlation between glucose and spurious factors that may exist with one subject is weakened by calibration using data from multiple subjects. A factor which is due to the environment/instrument that happens to be correlated with glucose during the measurement for one subject is likely to be correlated to glucose during measurements for multiple subjects.

Figure 7A:
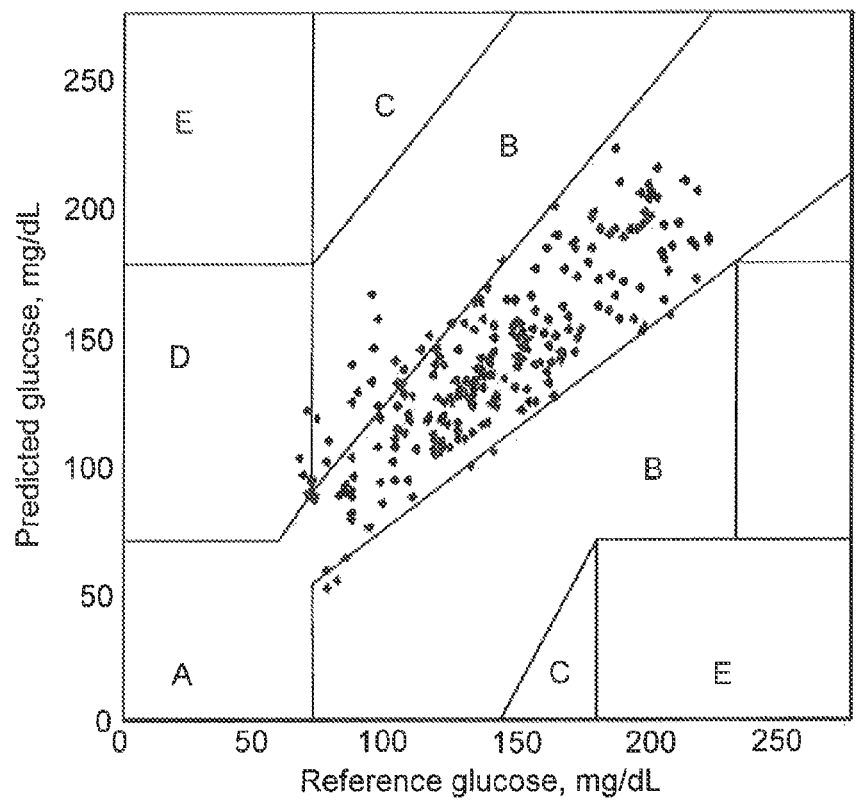
FIGS. 7a and 7b include: left (a): predicted vs. reference results using a common calibration algorithm generated on data from nine volunteers; the mean absolute error is 12.8% and the $R^2$ is 0.7; right (b): the calibration regression vector compared to the glucose spectrum; the correlation between the regression vector and the glucose spectrum is 0.45.
Figure 7B:
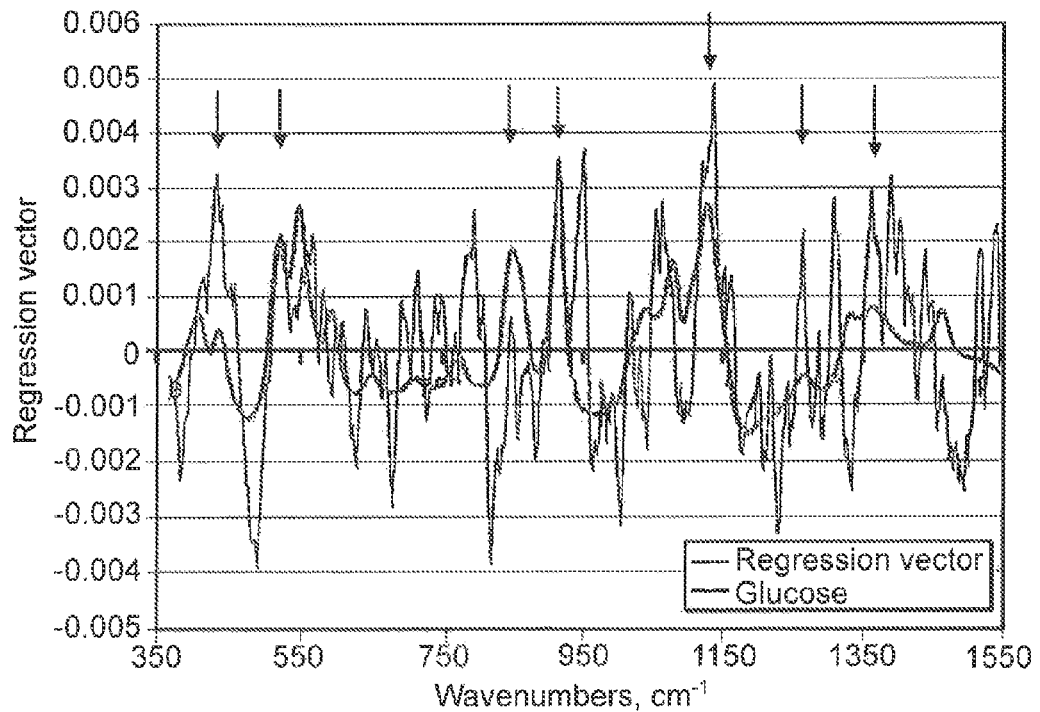

A calibration was generated on data comprising 244 samples from a group of nine subjects whose calibration quality is relatively high. The fact that the optimum number of factors for this calibration is 17 indicates that many differences among subjects are being accounted for. The results are shown in FIG. 7. A mean absolute error for this group of 12.86 and an $R^2$ of 0.7 is an indication that glucose is an important part of the calibration. Stronger evidence that this calibration is based on glucose is provided by observing the regression vector for the calibration on this data, also shown in FIG. 7. Many glucose spectrum peaks are seen in the calibration regression vector. The strong calibration between the regression vector and the glucose spectrum of 0.45, even though there are 17 factors, indicates that the glucose signal is strong enough to be detected among the large variances in spectra that occur among 9 different subjects. This indicates that glucose is being measured.

Figure 8A:
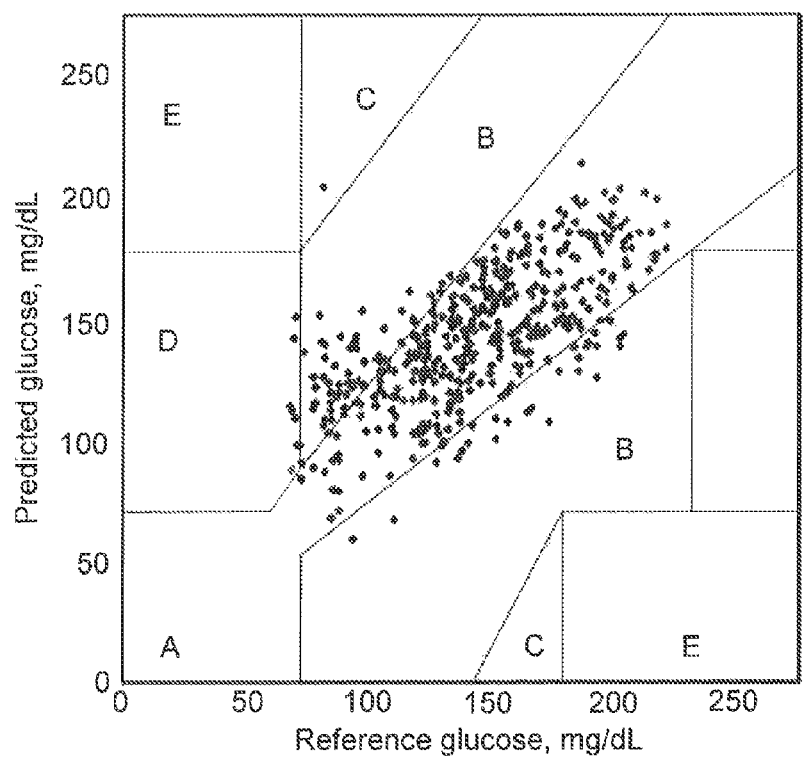
FIGS. 8a and 8b include: left (a): predicted vs. reference results for all 17 volunteers combined into one calibration group; the MAE is 16.9%; right (b): the calibration regression vector compared to the glucose spectrum; many peaks of glucose can be observed in the regression vector.
Figure 8B:
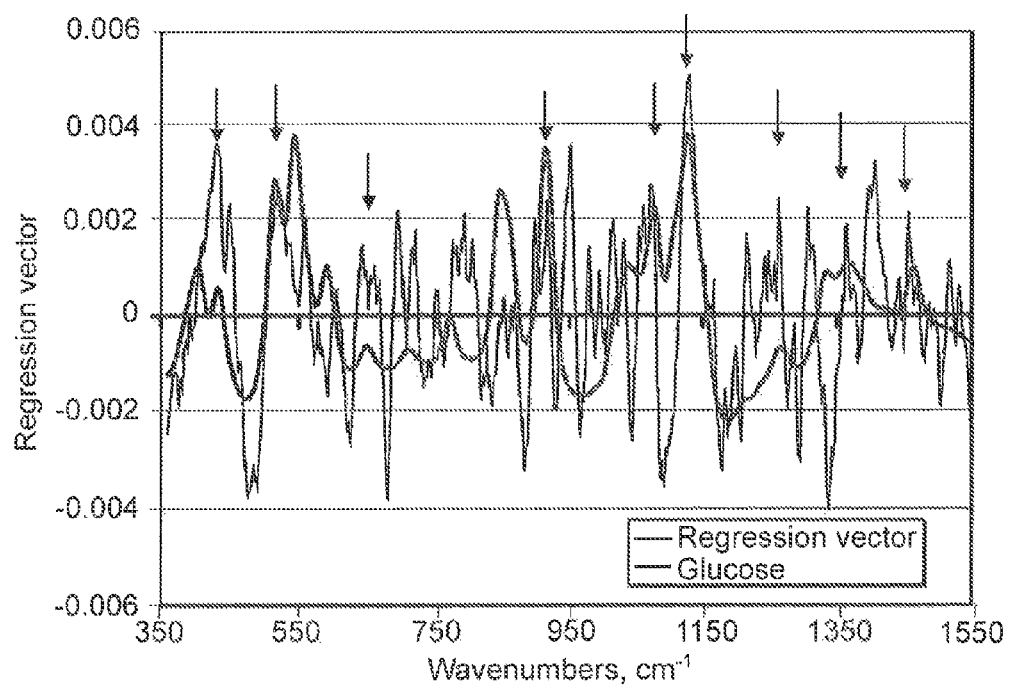

When data from all 17 subjects are combined into one group, the average error grows to 16.9%. A very positive result in that even with this data set, the regression vector includes many peaks of glucose, as is shown in FIG. 8. Even though many more parameters are changing, as indicated by a model with 21 factors, the correlation between the regression vector and the glucose is being measured.

The signal to noise ratio (SNR) can be calculated as the ratio of the collected signal to the noise at each wavenumber (for a 3 minute measurement, for example) averaged across the spectral measurement range. More specifically, at each pixel along the wavenumber axis, the SNR was calculated by dividing the intensity of the combined background and Raman signal by an estimate of the noise of that signal. The SNR's at each pixel were averaged across the spectral measurement range, 355 to 1545 $cm^{-1}$ to obtain an averaged result. The actual SNR varied somewhat with each subject.

The intensity of the background signals can change (typically decreased) during the course of a measurement. In the example where each spectrum was formed by averaging 90 consecutive two-second acquisitions (frames), calculation of the noise in the signal by the method of calculating the standard deviation of the above averages, results in a high estimate of the noise because the change due to the background signal (decrease) is high relative to the size of the random noise. To obtain a better estimate of the random noise, the standard deviation at each pixel was calculated across 90 frames for one measurement. The changing background signal has less of an effect over the time frame of one spectrum (3 minutes) than it does over the duration of the entire measurement. The estimate of noise was then calculated by dividing this by $\sqrt{90}$.

The basis for this is a statistical relationship. For random noise the standard deviation of a series of means (each an average of 90 acquisitions) is the standard deviation of the individual measurement (acquisitions) divided by the square root of the number of measurements used to calculate the means (90).

For a shorter measurement in which there is little or no change in the background signal, a simple calculation of the standard deviation can be used to estimate the noise level. Alternatively, a periodic system reference measurement can also be used to determine the noise level for each patient or group of patients.

Unlike a monochromator, in a multi-channel spectrometer the exit slit is removed and the single-channel detector is replaced by an array detector. For certain applications, a charge coupled device (CCD) camera is used to exploit the vertical dimension for better sensitivity. Light throughput is basically doubled (neglecting vignetting effect) when twice the CCD pixel rows are used. As a liquid nitrogen cooled CCD is operated within a shot noise limited regime, doubling the number of pixel rows equivalently increases the signal to noise ratio (SNR) by ~1.4X in this example. For non-imaging and low signal measurements, this way of "vertical binning" has been an effective way to obtain better SNR without increasing laser power or changing collection optics. The primary function of the 4 f imaging system is to image the entrance slit at the CCD plane. The grating inserted in the Fourier plane disperses different light frequencies into different spatial frequencies. An elongated entrance is needed to fully utilize the vertical dimension of the CCD camera. High Numerical Aperture (NA) is usually employed to further improve the system throughput and compactness simultaneously. The combination of these two factors elongated slit and high NA contributes to a significantly curved image at the CCD plane. In general an f number below 2.0 is preferred and preferably about 1.4. If vertical binning is applied naively, the resolution of the resulting spectrum is highly degraded. The degree of degradation depends, for example, on the length of vertical binning performed.

By increasing the size and resolution of the imaging-device to over one million pixels, increasing the number and size of optical fibers for coupling to the detector, the use of a side-looking parabolic mirror and curvature correction during binning, substantial improvements in signal to noise measurement can be made.

Note also, in addition to curved slit imaging, however, slit elongation and high NA optics together make the problem more significant. One option for addressing this issue involves adopting curved slits, employing convex spherical gratings, and using off-axis compensating entrance optics. Also, a fiber bundle can be employed as a shape transformer to increase light collection efficiency. One end of the fibers is arranged into a round shape to fill up the focal spot. On the other end, fibers are patterned into a linear array serving as the entrance slit. If instead a linear shape is arranged, a reversed curved shape which counteracts the curvature introduced by the optical system can correct the problem to the first order. A preferred embodiment however uses a software approach which is equivalent to the method of employing the curved fiber bundle at the entrance slit when curvature correction is needed. This method involves using a reference material which gives a sharp image of the curved slit. Measuring the curvature of the slit image around the center wavelength indicates how much the (vertically) off-center CCD rows have to be shifted horizontally. This method, as well as the curved fiber bundle approach, ignores the fact that the slit image curvature is a function of wavelength. Since the Raman signal returning from the illuminated portion of the skin is a small part riding on a large fluorescence background even when near infrared (NIR) excitation is employed, light throughput considerations indicate a performance for the use of a large CCD imager that is greater than one inch in height (1340×1300 pixels). With this size of CCD camera, the slit image curvature correction is not fully satisfactory.

Figure 9:
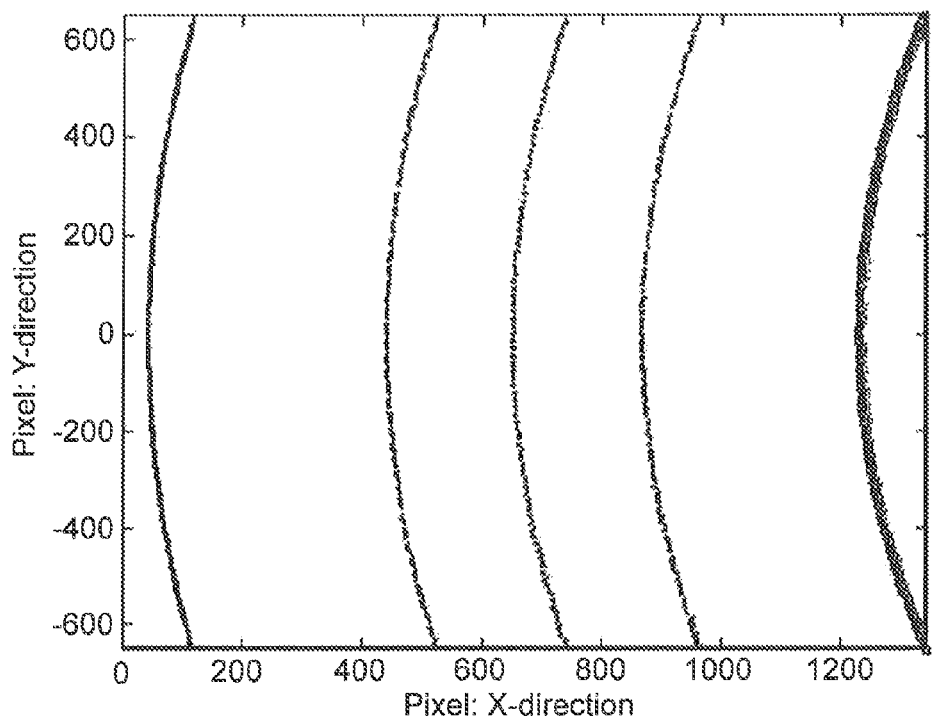
FIG. 9 illustrates the impulse response of the system at 5 different wavelengths for an infinitesimally narrow slit for a CCD with 1340 (H)×1300 (V) pixels with a 20 μm$^2$ pixel size "-" is at 830 nm, "- -" is at 880 nm, ". . ." is at 905 nm, "-. - ." is at 930 nm and "Φ" is at 970 nm.
Figure 10:
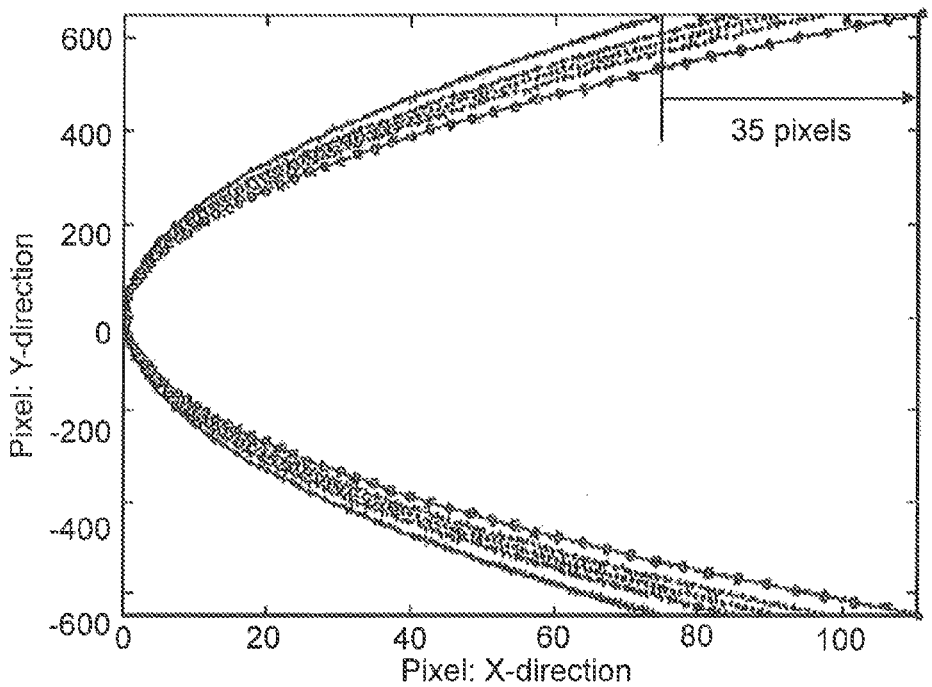
FIG. 10 illustrates curves in FIG. 9 shifted to apexes where the largest difference is 35 pixels across the CCD.
Figure 11:
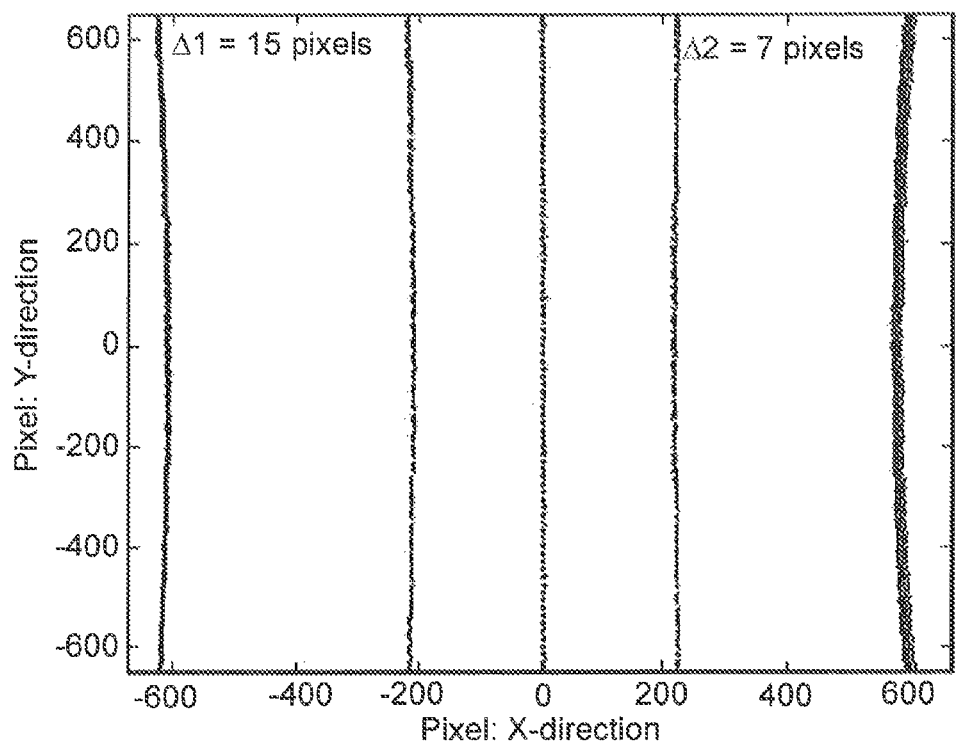
FIG. 11 shows the first order correction in which the uncorrected error is still ~15 pixels at both sides of the CCD where "-" is at 830 nm, "- -" is at 880 nm, ". . ." is at 905 nm, "-. - ." is at 930 nm and "Φ" is at 970 nm.

The imaging system of a simple dispersive spectrometer is composed of a 4 $f$ system with a diffraction grating at the Fourier plane. Starting with the grating equation:

$$\sin\alpha + \sin\beta = \frac{m\lambda}{\rho} \quad (2)$$

where $\alpha$ and $\beta$ are incident and diffraction angles, m is the diffraction order, $\lambda$ is the wavelength, and p is the grating pitch. Notice that his equation considers only the plane waves with $\vec{K}_{in}\vec{K}_{out}$ in place with the grating vector $\vec{K}_g$. For any plane wave that emerges at an angle $\theta$ with respect to the plane spanned by the optical axis and the grating vector, the modified grating equation reads:

$$\sin\alpha + \sin\beta = \frac{m\lambda}{\rho} \quad (3)$$

where the cosine term is a result of light emerging at a height different than 0. Maximum practical slit height is determined by designing $\theta$ to be smaller than the NA of the system. Beyond that vignetting can be very serious and therefore detracts from gain in throughput. After Taylor expansion and keeping up to the second order term of cosine, diffraction angle as a function of $\theta$ is obtained:

$$\delta\beta = \frac{m\lambda\theta^2}{2\rho\cdot\cos\beta_0} \quad (4)$$

where $\beta_0$ is the diffraction angle of the center wavelength and $f$ is the focal length of the 4 $f$ system. To cast Equation 4 into the spatial coordinates x and y with paraxial approximation, substituting $\theta$ with $y_{CCD}/f$ and $\delta\beta$ with $x_{CCD}/f$ and the final equation is obtained:

$$\frac{x_{CCD}}{f} = \frac{m\lambda\cdot\left(\frac{y_{CCD}}{f}\right)^2}{2\rho\cdot\cos\beta_o}(1.4) \quad (5)$$

with specifications from the Raman spectroscopic system for in vivo blood analytes concentration measurements, the CCD is ~1 inch$^2$ in size with 20 µm$^2$ pixel size, and focal length of the 4 $f$ system is 7.5/8.5 cm. With laser excitation at 830 nm, the spectral range of Raman signal measurements is from 830-970 nm. The impulse response (for an infinitesimally narrow slit) of the system is plotted in FIG. 9 for 5 wavelengths over the spectral range. To better compare the curves for different wavelengths, the 830 nm line is used as a reference and all other curves are shifted left to align all vertexes as shown in FIG. 10. "Vertical binning" without dealing with the curvature results in a virtually useless spectrum (~36 pixels FWHM resolution). With the prior method by simply shifting bins assuming the curvature stays the same over the whole spectral range results in errors shown in FIG. 11. The curvature induced error can be as large as ±15 pixels off the correct position for the both ends of the CCD even after the first attempt by either the prior method or the curved bundle method.

With an in vivo Raman system, a fiber bundle was chosen to maximize the effective sample area of Raman signal collection. The fiber bundle (Romack Inc.) is composed of 65 cladding stripped fibers with 400 µm core diameter. The linear exit end serves as the entrance slit with an equivalent dimension of 26(H)×0.4(V) mm and is imaged ~1.1X at the CCD (Roper Scientific) plane. The pixel dimension of the CCD is 1340(H)×1300(V) with 20×20 µm$^2$ pixel size. A Kaiser HoloSpec $f$/1.4 spectrometer was slightly modified to fit in the fiber bundle but the setup of the imaging optics and grating was intact. The prior method measures the image curvature at one wavelength and uses it to shift off-center rows correspondingly and therefore the fact that the curvature increases towards the higher dispersion end is completely ignored. To further reduce errors, due to the curvature change over the spectral range, each row spectrum is "stretched" by various amounts compared to the (vertically) center pixel row. That means that the same spectral coverage occupies a different number of pixels in different rows. The (vertically) center row has the fewest number of pixels whereas the top or bottom row has the most. Therefore a linear shifting strategy does not give perfect correction.

Figure 12:
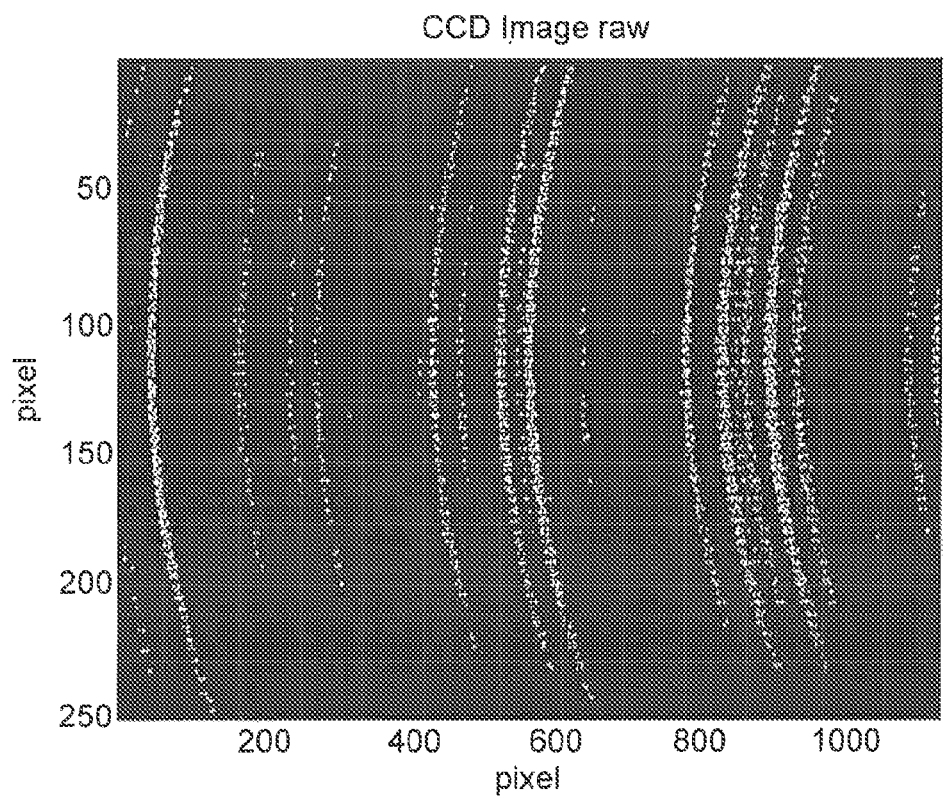
FIGS. 12-14 show CCD images of acetaminophen powder (5 pixel hardware binning) after correction using the first method using the center wavelength and the second method using several spectral lines and interpolation, repeating.
Figure 13:
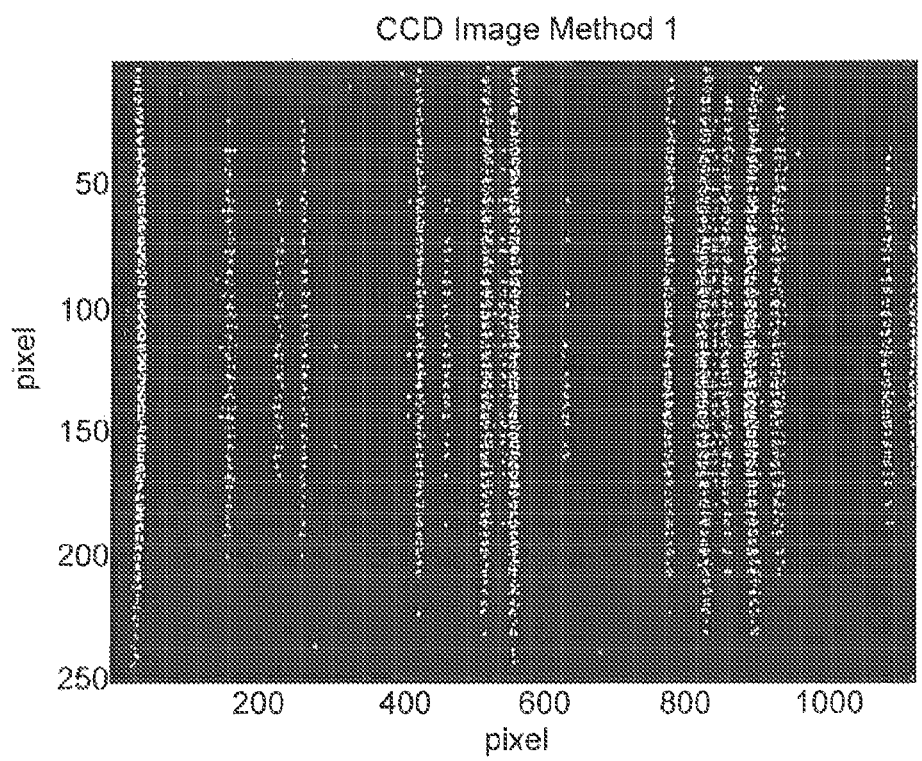
Figure 14:
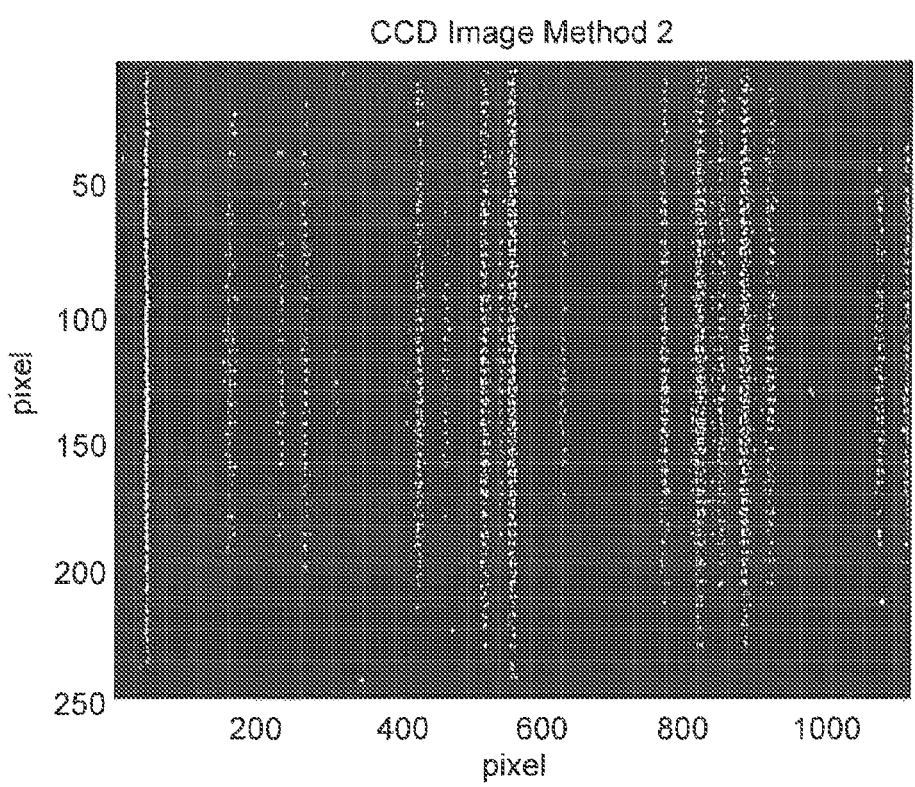

In the preferred method, instead of using one spectral line, i.e., measuring the curvature of one wavelength, several spectral lines are measured and used as boundaries to separate the row spectra into several segments. Those chosen peaks are then aligned with the respective ones in the (vertically) center row spectrum. Linear interpolation is incorporated to "compress" the spectra back to the same length as the center row spectrum in each segment, while maintaining energy conservation. Finally the compressed row spectra are summed and result in the final spectrum. The raw and corrected slit images with prior and preferred methods with data of acetaminophen powder are shown in FIGS. 12-14 for comparison. Notice that the images were taken with 5-pixel hardware binning to reduce the amount of data. The curvature error introduced by the hardware binning is on average less than 1 pixel and thus negligible. The FWHM linewidth reduction is 7% from the prior to the preferred method.

Figure 15:
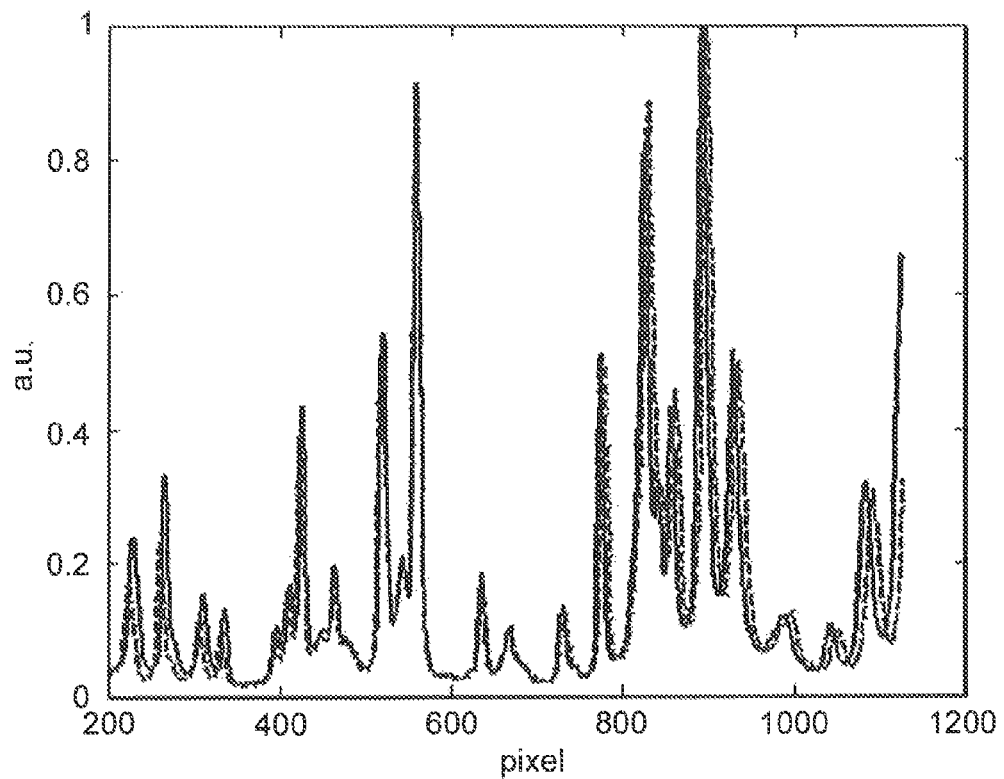
FIGS. 15 and 16 both show comparison of two spectra ("-" center, "- -" top) after the first and second methods, respectively.
Figure 16:
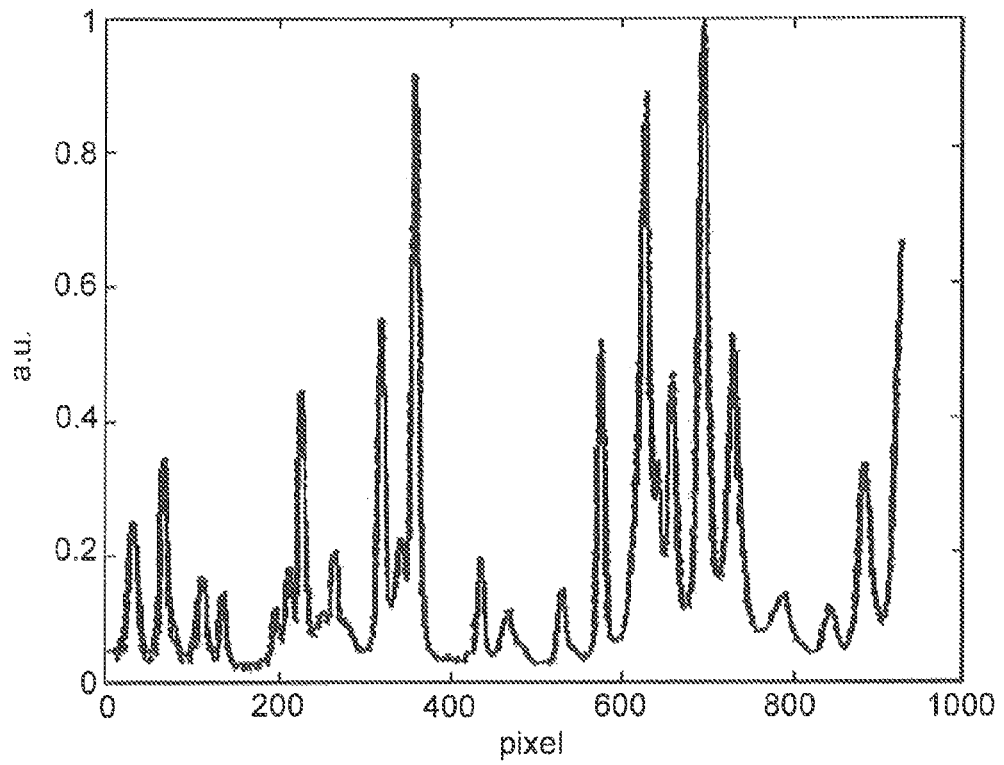

Two methods thus involve curvature calibration and correction. A full image is first taken with a reference material which has prominent peaks across the spectral range. The material in this example is acetaminophen powder. The calibration method generates a map and a scale factor for the correction method which uses the information to correct future measurements. By integrating the two software programs written in Matlab (Mathworks, Inc.) with Labview (National Instrument) data acquisition software, the correction time is less than 50 milliseconds and can be used for real-time application with 2-second integration time per frame. One important issue in implementation is how accurately those peaks serving as separation boundaries can be identified. Using simulated scenarios for different amounts of random noise, generally the peaks with sharper tips and higher SNRs are more resistant to noise distortion. This, for practial implementation the reference material has to be properly chosen and the reference image must have superior SNR. One way to visually evaluate the correction result is comparing the processed spectra of two far separated rows. In FIG. 15 the center row spectrum is compared to the top row from the prior method. The uncorrected errors show up as wavelength drifts and because the curvature of the center wavelength was used for correction, the leftover errors become more significant towards two sides. Spectra from the same two rows are compared after the preferred method. The evidence of wavelength drift is greatly reduced and the discrepancies are mainly manifested in intensity differences which probably results from vignetting.

For better system throughput, an elongated slit is generally employed in a high NA dispersive spectrometer. Due to out-of-plane light incident at the grating, the slit image becomes approximately a parabola. Naively binning vertical pixels worsens resolution if precaution has not been taken. The curvature formation arises from out of plane diffraction results in measurement errors for the system. A fiber bundle shape transformer has been a useful tool for shape matching to maximize light collection efficiency. One way to reduce the image curvature is to make the shape of the fiber bundle also curved but in the other direction to counteract the optical distortion. A software-based approach was employed in the present in vivo Raman spectroscopic system. Significant improvement was obtained after such first order correction, however, due to the truly elongated nature of this system. A preferred embodiment of the present invention includes a method which acknowledges the fact that image curvature is wavelength dependent and uses linear interpolation to resample the row spectra while maintaining energy conservation. The results show that this method indeed gives better correction compared to the previously described method. The overall linewidth reduction is 7% for the acetominophen spectrum used as an example. The correction time is ~50 msec and therefore real-time curvature correction is achievable with this software method.

The claims should not be read as limited to the described order or elements unless stated to that effect. Therefore, all embodiments that come within the scope and spirit of the following claims and equivalents thereto are claimed as the invention.

What is claimed:

1. A method of processing Raman spectral data comprising:
   obtaining an array of Raman spectral data collected through a first skin layer of a patient;
   binning the Raman spectral data;
   comparing the binned Raman spectral data from the first skin layer with measured Raman spectral data from a second skin layer underlying the first layer, the Raman spectral data including a plurality of analytes within at least one of the first skin layer and the second skin layer; and
   based on said comparing step, determining a concentration of glucose within a region of tissue underlying the first skin layer with the measured Raman spectral data.

2. The method of claim 1 further comprising using a light delivery and collection system including a light source and a detector to collect the Raman spectral data.

3. The method of claim 1 further comprising providing Raman data having a signal to noise ratio of at least 2000.

4. The method of claim 1 further comprising collecting light with a side-looking parabolic mirror.

5. The method of claim 1 further comprising measuring a Raman spectrum of a dermal layer and comparing the dermal layer Raman spectrum to a reference spectrum.

6. The method of claim 1 further comprising measuring a reference spectrum for the subject and determining a signal to noise ratio for the subject.

7. The method of claim 1 further comprising detecting the Raman shifted light with a binning detector.

8. The method of claim 1 further comprising measuring a concentration of glucose in the patient's blood.

9. The method of claim 1 further comprising performing curvature correction of Raman spectral data as a function of wavelength with a software program.

10. The method of claim 1 further comprising coupling light from a mirror to a spectrometer with a fiber optic device.

11. The method of claim 1 further comprising forming a regression vector and comparing the regression vector to a glucose spectrum.

12. The method of claim 1 further comprising providing Raman spectral data having a signal to noise ratio of at least 6000.

13. The method of claim 1 further comprising detecting Raman scattered light for a period of less than 10 seconds to obtain the Raman spectral data.

14. The method of claim 1 further comprising providing a fiber optic coupler having a two dimensional array at a first end and a single row of fibers at a second end.

15. The method of claim 1 further comprising collecting the Raman spectral data from a blood sample within the second skin layer.

16. The method of claim 1 further comprising controlling a temperature of a dispersing element that spatially disperses light onto a detector having at least 1 million pixel elements.

17. The method of claim 16 wherein the dispersing element comprises a grating.

18. The method of claim 1 further comprising delivering light having a wavelength in a range of 750 nm to 1050 nm from a laser through a mirror onto a sample to be measured, the mirror collecting light from the sample.

19. The method of claim 18 further comprising sampling light from the laser with a detector to monitor light incident on the sample.

20. The method of claim 1 further comprising cooling a detector with a thermoelectric cooler.

21. The method of claim 1 further comprising comparing a measured Raman spectrum of a dermal layer with spectral features of a plurality of dermal layers and determining a dermal layer from which the spectrum is acquired.

22. The method of claim 1 further comprising determining an error value for the glucose concentration.

23. A method of processing Raman spectral data comprising:
obtaining an array of Raman spectral data collected through a first skin layer of a patient;
processing the Raman spectral data;
comparing the processed Raman spectral data from the first skin layer with measured Raman spectral data from a second skin layer underlying the first layer; and
based on said comparing step, determining a concentration of glucose within a region of tissue underlying the first skin layer with the measured Raman spectral data.

24. The method of claim 23 further comprising using a partial least squares regression to analyze the Raman spectral data.

25. The method of claim 23 further comprising determining an error value for the measure glucose concentration.

26. The method of claim 23 further comprising illuminating the region of tissue with infrared light emitted by a laser.

* * * * *